(12) United States Patent
Gitterle et al.

(10) Patent No.: US 9,682,150 B1
(45) Date of Patent: Jun. 20, 2017

(54) ANTI-AGING NUTRITIONAL SUPPLEMENT COMPOSITIONS FOR ANIMALS

(71) Applicant: NextGen Research, Greenville, SC (US)

(72) Inventors: Marcus Louis Gitterle, Greenville, SC (US); Bevan Craig Elliott, Greenville, SC (US); Jonathan David Griffith, Greenville, SC (US)

(73) Assignee: NextGen Research, Greenville, SC (US)

( * ) Notice: Subject to any disclaimer, the term of this patent is extended or adjusted under 35 U.S.C. 154(b) by 0 days.

(21) Appl. No.: 14/507,125

(22) Filed: Oct. 6, 2014

Related U.S. Application Data

(60) Provisional application No. 61/886,769, filed on Oct. 4, 2013, provisional application No. 61/886,770, filed on Oct. 4, 2013.

(51) Int. Cl.
| | |
|---|---|
| *A61K 31/105* | (2006.01) |
| *A61K 31/122* | (2006.01) |
| *A61K 31/202* | (2006.01) |
| *A61K 31/409* | (2006.01) |
| *A61K 47/44* | (2006.01) |
| *A61K 47/48* | (2006.01) |
| *A23K 1/18* | (2006.01) |
| *A23K 1/16* | (2006.01) |
| *A23K 1/165* | (2006.01) |
| *A61K 31/05* | (2006.01) |

(52) U.S. Cl.
CPC .......... *A61K 47/48015* (2013.01); *A23K 1/16* (2013.01); *A23K 1/164* (2013.01); *A23K 1/1646* (2013.01); *A23K 1/1653* (2013.01); *A23K 1/1806* (2013.01); *A61K 31/05* (2013.01); *A61K 31/122* (2013.01); *A61K 31/202* (2013.01); *A61K 31/409* (2013.01); *A61K 47/44* (2013.01)

(58) Field of Classification Search
CPC ................ A61K 9/5169; A61K 9/5192; A61K 2300/00; A61K 38/168; A61K 38/1866; A61K 31/343; A61K 38/1841; A61K 38/2013; A61K 38/39; A61K 47/24; A61K 47/40; A61K 47/48176; A61K 2800/522; A61K 8/4926; C12Q 1/6804; C12Q 2565/113; C12Q 1/6834; C12Q 1/6848; C07H 21/00; C07D 471/06
See application file for complete search history.

(56) References Cited

U.S. PATENT DOCUMENTS

| | | | | |
|---|---|---|---|---|
| 2008/0260849 | A1* | 10/2008 | Aimi et al. | A61K 9/5169 424/499 |
| 2010/0150853 | A1* | 6/2010 | Cassin et al. | A61K 8/19 424/59 |
| 2011/0250178 | A1* | 10/2011 | Brooks et al. | A61K 8/922 424/93.1 |

OTHER PUBLICATIONS

Ikeda, J. Incl Phenom Macrocycl Chem (2013) 77:49-65, "Water-soluble fullerenes using sol. agents, and their appl . . . " published Apr. 24, 2013.*

* cited by examiner

*Primary Examiner* — Debbie K Ware
(74) *Attorney, Agent, or Firm* — Dinsmore & Shohl LLP

(57) ABSTRACT

Anti-aging nutritional supplements for animals contain, in a carrier oil base, a carbon-60 fullerene compound or complex, biologically active phenols or polyphenols, asthaxanthin, chlorophyll or a chlorophyll derivative, coenzyme Q10, and mixed tocopherols and tocotrienols.

19 Claims, No Drawings

ANTI-AGING NUTRITIONAL SUPPLEMENT COMPOSITIONS FOR ANIMALS

CROSS-REFERENCES TO RELATED APPLICATIONS

The present application claims the benefit of priority under 35 U.S.C. §119(e) to U.S. Provisional Application Ser. No. 61/886,769, filed Oct. 4, 2013, and also to U.S. Provisional Application Ser. No. 61/886,770, filed Oct. 4, 2013.

TECHNICAL FIELD

The present specification relates generally to nutritional supplement compositions for animals and, more specifically to nutritional supplement compositions for animals that inhibit or reverse the physiological effects of aging in the animals.

BACKGROUND

Natural selection has allowed some animals to possess some more skills than others that help them in the process of everyday life. Small animals must stay alert and in control of their surroundings to survive. Unluckily, some small animals do have trouble surviving and staying in good health, unless they consumed a type of nutritional supplement to prolong their lifespan.

Animals typically experience different aging processes compared to that of the human species. Animals come in different sizes, shapes, colors, and other characteristics, but one similar trait for all living beings is that each species age appropriately. When separating animal groups into sizes, small animals often share a common bond with each other in the animal kingdom. Small animals must be defensive when it comes to such aspects as movement and attention. Small animals must be able to protect themselves from larger beings, as well as still provide for their offspring.

Horses have been utilized by human civilizations throughout history. Horses have had many different uses to assist humans in advancing society. The versatility that horses have shown throughout time has exemplified the qualities of the species. The daily habits of horses, both now and then, have always been demanding to a horse's health and well-being. Horses must remain in proper shape and fitness to complete common tasks, and may experience unforeseen health issues naturally without the proper nutritional supplements.

There remain ongoing needs for improved nutritional supplements for animals, such as small domesticated animals and horses, that mitigate or reverse the effects of aging.

SUMMARY

Against the above background, the present application is directed to anti-aging nutritional supplements for animals, particularly non-human animals. The anti-aging supplements according to embodiments herein may act as primarily as an antioxidant, cellular mitochondrial and electron transport chain revitalizer, and immune system booster, thereby improving the organism's response to toxins, fighting against inflammation, and decreasing other symptoms of aging.

Additional features and advantages of the embodiments described herein will be set forth in the detailed description which follows, and in part will be readily apparent to those skilled in the art from that description or recognized by practicing the embodiments described herein, including the detailed description and claims which follow. It is to be understood that both the foregoing general description and the following detailed description describe various embodiments and are intended to provide an overview or framework for understanding the nature and character of the claimed subject matter.

DETAILED DESCRIPTION

References will now be made in detail to embodiments of anti-aging nutritional supplements for animals. In general, the anti-aging nutritional supplements according to embodiments herein are not intended for human use. The anti-aging nutritional supplements according to embodiments herein may be used for non-human animals including, but not limited to, horses, dogs, cats, rabbits, hamsters, and other small mammals.

According to some embodiments, a nutritional supplement for animals may include a carrier oil base, carbon-60 fullerene ($C_{60}$), biologically active phenols and polyphenols from various natural sources, astaxanthin, chlorophyll and/or chlorophyll derivatives, coenzyme Q10, and mixed tocopherols and tocotrienols. In some embodiments, the nutritional supplement may further include docosahexaenoic acid (DHA), eicosapentaenoic acid (EPA), or both. The ingredients of the nutritional supplement may be dissolved or reacted in a carrier oil base to form the nutritional supplement. In some embodiments, the nutritional supplement is an oily liquid.

The carrier oil base may be any oil that is digestible and non-toxic to animals. In non-limiting examples, the carrier oil base may be chosen from olive oil, argan oil, fish oil, hill oil, medium-chain triglycerides, and combinations thereof.

The carbon-60 fullerene may be derived from any natural or synthetic source. For example, the carbon-60 fullerene may be synthetically formed in a laboratory or may be acquired from natural sources such as soot, carbon black, molasses, shungite, shilajit, or meteoric solids.

The biologically active phenol or polyphenol may include compounds such as oleuropein, tyrosol, hydroxytyrosol, oleocanthal, catechol, vanillic acid, catechins, or mixtures thereof, for example. Compounds such as oleuropein, tyrosol, hydroxytyrosol, and oleocanthal may be derived from the olive tree, for example, from olive leaf, olive fruit, or olive oil. Compounds such as oleuropein, tyrosol, catechol, vanillic acid, and catechins may be derived from argan oil, for example. Other sources of phenols and polyphenols include fruits, seeds, and nuts.

The astaxanthin may be derived from microalgae or any other suitable source.

Chlorophyll and chlorophyll derivatives may be acquired from any suitable source by any suitable technique. For example, chlorophyll and chlorophyll derivatives may be acquired from olive oil, chlorella, spinach, and other green leafy vegetables.

In some embodiments, the coenzyme Q10 may be present in the nutritional supplement in the form of ubiquinone, semiquinone, ubiquinol, or combinations thereof.

In some embodiments, the mixed tocopherols and tocotrienols in the nutritional supplement may be derived from vegetable oils, for example.

When present in the nutritional supplement, DHA, EPA, or both, may be derived from fish oil, microalgae, or a combination thereof, for example.

In the nutritional supplement according to some embodiments, at least a portion of the carbon-60 fullerene is present in the nutritional supplement as one or more biologically active covalent fullerene compounds or non-covalent fullerene complexes. In some embodiments, all of the carbon-60 fullerene may be present in the nutritional supplement as one or more biologically active covalent fullerene compounds or non-covalent fullerene complexes.

In some embodiments, the nutritional supplement may contain at least one covalent carbon-60 fullerene compound. Non-limiting examples of covalent carbon-60 fullerene compound include covalent fullerene-fatty acid triglyceride compounds.

In some embodiments, the nutritional supplement may contain at least one non-covalent carbon-60 fullerene complex. Non-limiting examples of non-covalent carbon-60 fullerene complexes include non-covalent fullerene-fatty acid triglyceride complexes, non-covalent fullerene-phenol/polyphenol complexes, non-covalent fullerene-porphyrin complexes, non-covalent fullerene-astaxanthin complexes, non-covalent fullerene-CoQ10 complexes, and combinations thereof.

In some embodiments, the nutritional supplement may contain at least one mixed non-covalent carbon-60 fullerene complex. Non-limiting examples of mixed non-covalent carbon-60 fullerene complexes include mixed non-covalent fullerene-polyphenol-triglyceride complexes, mixed non-covalent fullerene-chlorophyll-triglyceride complexes, mixed non-covalent fullerene-astaxanthin-triglyceride complexes, mixed non-covalent fullerene-CoQ10-triglyceride complexes, and combinations thereof.

In some embodiments, the nutritional supplement may contain a combination of at least two carbon-60 fullerene compounds chosen from covalent carbon-60 fullerene compounds, non-covalent carbon-60 fullerene complexes, and mixed non-covalent carbon-60 fullerene complexes.

According to some embodiments, the nutritional supplement may be an oil-based composition, in which the at least one biologically active covalent carbon-60 fullerene compound or non-covalent carbon-60 fullerene complex, the at least one biologically active phenol or polyphenol, the astaxanthin, the chlorophyll or chlorophyll derivative, the coenzyme Q10, and the mixture of biologically active tocopherols and tocotrienols are dissolved in the carrier oil base. One or more ingredients may react with or form complexes or compounds with each other while being dissolved in the carrier oil base, or after a period of time. The nutritional supplement may be prepared by combining a carrier oil mixture with the additional ingredients to dissolve or react the ingredients. The combining of ingredients may be carried out using ordinary mixing techniques under suitable temperature and pressure conditions.

In some exemplary embodiments, the nutritional supplement is oil-based and contains, based on the total volume of the nutritional supplement composition, a carbon-60 fullerene concentration of from 0.1 g/L to 1.6 g/L; a phenolic concentration of from 400 ppm to 4000 ppm; a chlorophyll concentration of from 10 ppm to 4000 ppm; an astaxanthin concentration of from 0.3 g/L to 3.0 g/L; a coenzyme Q10 concentration of from 0.2 g/L to 1 g/L; and a tocopherol/tocotrienol concentration of from 2 g/L to 20 g/L. The carbon-60 fullerene concentration is based on total weight of carbon-60 fullerenes alone, even if the carbon-60 fullerenes are complexed or covalently bound to another ingredient of the composition. The phenolic concentration is based on the total number of biologically active phenols and polyphenols present in the nutritional supplement. The tocopherol/tocotrienol concentration is based on the total amount of tocopherols and tocotrienols present in the nutritional supplement.

The nutritional supplement according to embodiments herein may be administered to an animal in any practical manner. For example, the nutritional supplement, particularly in an oil-based composition, may be administered to an animal orally or may be mixed with the animal's food so that oral administration occurs when the animal eats the food. The nutritional supplement may be administered in an amount effective to provide a quantifiable improvement in any ailment, condition, or malady the animal may have that is directly or indirectly attributable to aging.

It is believed that nutritional supplement compositions according to embodiments herein may affect cellular aging processes in an animal. The nutritional supplements begin working immediately to restore function, energy and vitality. With a once daily application to an animal's preferred dry or moist food source the nutritional supplement compositions may restore cellular energy through an anti-oxidant function that benefits vulnerable cells and tissues where aging has the deepest effects. It is believed that the nutritional supplement further may protect cell membranes.

Without intent to be bound by theory, it is believed that cells or animals are constantly exposed to attack by free radicals in the environment. Free-radicals are molecules that contain an extra "unpaired" electron. These unpaired electrons are like buzz saws, capable of damaging delicate cellular machinery by oxidation. It is believed that animal cells have built-in mechanisms for quenching these free-radicals but that over time this ability wanes, and fewer and fewer of the free-radical defense molecules are produced. As defenses wane, cellular systems are increasingly challenged and ultimately overtaxed by accumulating free-radical damage.

Anti-oxidants are often touted as the answer to free-radicals and cellular degeneration brought about by aging. Yet, conventional anti-oxidants do not provide much real-world protection against the constant onslaught of free radical attack. In particular, conventional anti-oxidants are completely used up by quenching just one free-radical. What is worse, each anti-oxidant molecule becomes a free-radical itself, by taking on the unpaired electron it quenched. Instead of helping, conventional anti-oxidants simply "kick the can down the road," by becoming another, only slightly more benign free radical. Without intent to be bound by theory, it is believed that the complexes within the nutritional supplements according to embodiments herein, unlike conventional anti-oxidants, hold on to free-radicals without reacting with them. As such, the complexes never take on an unpaired electron, and never themselves becomes a free-radical. Remarkably, individual complexes in the nutritional supplements according to embodiments herein can have ability to manage dozens of free-radicals at the same time. That is, the individual complexes do not react with the free-radicals, while retaining full function to do battle with the next group of otherwise damaging free-radicals. Moreover, by more effectively handling free radicals generally, the complexes in the nutritional supplements described herein provide protection to all cell types. It is known that free-radicals do not discriminate between cell types to attack. Comprehensive tissue protection against free radicals means that vulnerable brain, heart, skin, lung, kidney, muscle, bone, digestive system, liver, and other cell types are effectively protected from damage.

The mitochondria are the energy producing machines in animal cells. Without properly functioning mitochondria, cells do not have enough energy to carry on normal functions, defend themselves against oxidation, and perform the cellular cleanup activities necessary for peak functioning. As animals age, the number of energy creating mitochondria diminishes over time. Remaining mitochondria also become increasingly dysfunctional. These "old" mitochondria produce less energy and also generate more free-radicals. They are very much like an old car that gets less miles per gallon, while putting out more smog. This mitochondrial "smog" places further burdens on cellular energy metabolism, by increasing the need for free-radical quenching and protection. As free radical protection wanes with age, so also do mitochondria decline and become more and more dysfunctional, creating a downward spiral of cellular decline. The cellular decline is called "aging."

Without intent to be bound by theory, it is believed that the nutritional supplements according to embodiments herein have high affinity for the mitochondrial membrane, where the damaging free-radical mitochondrial smog is created. The mitochondrial membrane is where key cellular action is, when it comes to age reversal. It is believed that the complexes in the nutritional supplements according to embodiments herein improve cellular energy production by managing mitochondrial free-radicals where they are produced. Thus, in addition to quenching this mitochondrial pollution, the complexes also improve mitochondrial efficiency and cellular-energy balance.

Cell membranes are important to cellular health. They not only protect the delicate and complex mechanisms of life contained within, but they also function as master gatekeepers, carefully controlling what goes in and what can leave cells. Membranes are also important to cell-cell communication, which in turn are integral to maintenance of tissue and organ health. Without healthy cellular membranes, a cell cannot function normally, and it quickly dies. As animals age, cell membranes become more vulnerable to free-radical attack. In addition, due to their complexity, the cell membranes require large amounts of energy to maintain and protect. By providing essential Omega 3 fats required to maintain high-functioning membranes, the nutritional supplements according to embodiments herein help powerfully restore function to membranes, allowing these gatekeepers to function optimally, further protecting and enhancing cellular function.

The complexes in the nutritional supplements described herein may restore lost function in at least four ways. First, by effectively managing free-radicals, the cell can focus on making repairs, rather than fighting ongoing damage. Second, because cells now have much more energy to work with, they can begin to perform long-term restorative maintenance that would have been impossible without the protection and enhancement provided by the nutritional supplements. By restoring function to cell membranes, all cellular function benefit from increased efficiency and optimization of nutrient transport and cellular defense and signaling mechanisms. Organ function becomes increasingly optimized as animals continue to receive the nutritional supplements, because organs are communities of cells. As cell function improves, the function of organs improves. As organ function improves, the function of body systems improves.

It is believed that the nutritional supplements described herein may extend to all body systems of an animal, including brain and nerve function, vision, hearing, taste and digestion, muscle, skin and bone, kidney and liver function, and glandular tissues. It is believed that the effects of the nutritional supplements described herein are cumulative and that extended use can result in steady improvement, depending on an animal's condition and age before the nutritional supplements are administered.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the appended claims or to imply that certain features are critical, essential, or even important to the structure or function of the claimed subject matter. Rather, these terms are merely intended to highlight alternative or additional features that may or may not be utilized in a particular embodiment.

What is claimed is:

1. A nutritional supplement for animals, the nutritional supplement comprising:
    a carrier oil base chosen from olive oil, argan oil, fish oil, hill oil, medium-chain triglycerides, or combinations thereof;
    carbon-60 fullerene ($C_{60}$) dissolved in the carrier oil base;
    at least one biologically active phenol or polyphenol dissolved in the carrier oil base and selected from the group consisting of oleuropein, tyrosol, hydroxytyrosol, oleocanthal, catechol, vanillic acid, catechins, and combinations thereof;
    astaxanthin dissolved in the carrier oil base;
    chlorophyll or a chlorophyll derivative dissolved in the carrier oil base;
    coenzyme Q10 dissolved in the carrier oil base;
    a mixture of biologically active tocopherols and tocotrienols dissolved in the carrier oil base; and
    at least one biologically active non-covalent carbon-60 fullerene complex dissolved in the carrier oil base.

2. The nutritional supplement of claim 1, wherein the at least one biologically active non-covalent carbon-60 fullerene complex comprises a non-covalent carbon-60 fullerene-fatty acid triglyceride complex.

3. The nutritional supplement of claim 1, wherein the at least one biologically active non-covalent carbon-60 fullerene complex comprises a non-covalent carbon-60 fullerene-phenol/polyphenol complex.

4. The nutritional supplement of claim 1, wherein the at least one biologically active non-covalent carbon-60 fullerene complex comprises a non-covalent carbon-60 fullerene-porphyrin complex derived from the carbon-60 fullerene and the chlorophyll or chlorophyll derivative.

5. The nutritional supplement of claim 1, wherein the at least one biologically active non-covalent carbon-60 fullerene complex comprises a non-covalent carbon-60 fullerene-astaxanthin complex.

6. The nutritional supplement of claim 1, wherein the at least one biologically active non-covalent carbon-60 fullerene complex comprises a non-covalent carbon-60 fullerene-CoQ10 complex.

7. The nutritional supplement of claim 1, wherein the at least one biologically active non-covalent carbon-60 fullerene complex comprises a mixed non-covalent carbon-60 fullerene-polyphenol-triglyceride complex.

8. The nutritional supplement of claim 1, wherein the at least one biologically active non-covalent carbon-60 fullerene complex comprises a mixed non-covalent carbon-60 fullerene-chlorophyll-triglyceride complex.

9. The nutritional supplement of claim 1, wherein the at least one biologically active non-covalent carbon-60 fullerene complex comprises a mixed non-covalent carbon-60 fullerene-astaxanthin-triglyceride complex.

10. The nutritional supplement of claim 1, wherein the at least one biologically active non-covalent carbon-60 fullerene complex comprises a mixed non-covalent carbon-60 fullerene-CoQ10-triglyceride complex.

11. The nutritional supplement of claim 1, wherein the astaxanthin is derived from microalgae.

12. The nutritional supplement of claim 1, wherein the chlorophyll or chlorophyll derivative is derived from olive oil, olive leaf, chlorella, spinach, a leafy green vegetable, or combinations thereof.

13. The nutritional supplement of claim 1, wherein the coenzyme Q10 is in the form of ubiquinone, semiquinone, ubiquinol, or combinations thereof.

14. The nutritional supplement of claim 1, further comprising DHA, EPA, or both.

15. A nutritional supplement composition comprising:
a carrier oil base selected from the group consisting of olive oil, argan oil, fish oil, hill oil, medium-chain triglycerides, and combinations thereof; and
at least one biologically active non-covalent carbon-60 fullerene complex dissolved in the carrier oil base, the at least one biologically active non-covalent carbon-60 fullerene complex chosen from mixed non-covalent carbon-60 fullerene-polyphenol-triglyceride complexes, mixed non-covalent carbon-60 fullerene-chlorophyll-triglyceride complexes, mixed non-covalent carbon-60 fullerene-astaxanthin-triglyceride complexes, mixed non-covalent carbon-60 fullerene-CoQ10-triglyceride complexes, and combinations thereof.

16. The nutritional supplement composition of claim 15, further comprising:
at least one biologically active phenol or polyphenol selected from the group consisting of oleuropein, tyrosol, hydroxytyrosol, oleocanthal, and combinations thereof;
carbon-60 fullerene ($C_{60}$) dissolved in the carrier oil base astaxanthin;
chlorophyll or a chlorophyll derivative;
coenzyme Q10; and
a mixture of biologically active tocopherols and tocotrienols.

17. The nutritional supplement composition of claim 16, comprising, based on the total volume of the nutritional supplement composition:
a carbon-60 fullerene concentration of from 0.1 g/L to 1.6 g/L;
a phenolic concentration of from 400 ppm to 4000 ppm;
a chlorophyll concentration of from 10 ppm to 4000 ppm;
an astaxanthin concentration of from 0.3 g/L to 3.0 g/L;
a coenzyme Q10 concentration of from 0.2 g/L to 1 g/L; and
a tocopherol/tocotrienol concentration of from 2 g/L to 20 g/L.

18. The nutritional supplement composition of claim 15, further comprising at least one biologically active phenol or polyphenol selected from the group consisting of oleuropein, tyrosol, hydroxytyrosol, oleocanthal, and combinations thereof, wherein the at least one biologically active non-covalent carbon-60 fullerene complex comprises a mixed non-covalent carbon-60 fullerene-polyphenol-triglyceride complex.

19. A nutritional supplement composition comprising:
a carrier oil base comprising olive oil, medium-chain triglycerides, or combinations thereof;
carbon-60 fullerene ($C_{60}$) dissolved in the carrier oil base;
at least one biologically active phenol or polyphenol dissolved in the carrier oil base and chosen from oleuropein, tyro sol, hydroxytyrosol, oleocanthal, and combinations thereof; and
at least one biologically active mixed non-covalent carbon-60 fullerene-polyphenol-triglyceride complex dissolved in the carrier oil base.

* * * * *

UNITED STATES PATENT AND TRADEMARK OFFICE
CERTIFICATE OF CORRECTION

PATENT NO. : 9,682,150 B1  
APPLICATION NO. : 14/507125  
DATED : June 20, 2017  
INVENTOR(S) : Marcus Louis Gitterle et al.

It is certified that error appears in the above-identified patent and that said Letters Patent is hereby corrected as shown below:

In the Claims

Column 6, Claim 1, Line 21:
"hill oil, medium-chain triglycerides, or combinations"
Should read:
--krill oil, medium-chain, triglycerides, or combinations--;

Column 7, Claim 15, Line 20:
"olive oil, argan oil, fish oil, hill oil, medium-chain"
Should read:
--olive oil, argan oil, fish oil, krill oil, medium-chain--; and Column 8, Claim 19, Line 33:
"oleuropein, tyro sol, hydroxytyrosol, oleocanthal, and"
Should read:
--oleuropein, tyrosol, hydroxytyrosol, oleocanthal, and--.

Signed and Sealed this  
Twenty-ninth Day of May, 2018

Andrei Iancu  
*Director of the United States Patent and Trademark Office*